United States Patent [19]
Morris

[11] Patent Number: 5,654,977
[45] Date of Patent: Aug. 5, 1997

[54] METHOD AND APPARATUS FOR REAL TIME DEFECT INSPECTION OF METAL AT ELEVATED TEMPERATURE

[75] Inventor: John W. Morris, Huntsville, Ala.

[73] Assignee: Teledyne Industries Inc., Los Angeles, Calif.

[21] Appl. No.: 382,526

[22] Filed: Feb. 2, 1995

[51] Int. Cl.$^6$ ................................................. G01N 25/72
[52] U.S. Cl. ................................................. 374/4; 374/124
[58] Field of Search ................................. 374/4, 5, 6, 7, 374/110, 121, 124, 128; 73/160; 250/341.6, 338.1; 364/507, 552, 557; 348/125, 130

[56] References Cited

U.S. PATENT DOCUMENTS

| | | | |
|---|---|---|---|
| 3,808,439 | 4/1974 | Renius | 374/4 |
| 4,118,732 | 10/1978 | Ichijima et al. | 358/101 |
| 4,319,270 | 3/1982 | Kimura et al. | 358/106 |
| 4,665,317 | 5/1987 | Ferriere et al. | 250/562 |
| 4,759,072 | 7/1988 | Yamane et al. | 382/8 |
| 4,958,307 | 9/1990 | Nishimura | 364/507 |
| 5,358,333 | 10/1994 | Schmidt et al. | 374/5 |

FOREIGN PATENT DOCUMENTS 2066482  7/1981  United Kingdom ............ 374/4

OTHER PUBLICATIONS

"New Defect–Detection System For A Rod and Bar Mill", Eisuke Yamanaka et al, pp. 1–14 (1993).

*Primary Examiner*—G. Bradley Bennett
*Attorney, Agent, or Firm*—Beveridge, Degrandi, Weilacher & Young

[57] ABSTRACT

A system for detecting, in real time, the existence, depth, extent, and type of a defect in an above ambient temperature object which has been formed by working or other heat input. Such defect detection is performed by analyzing IR emissions from the product, and from a defect site in particular, in order to assess the characteristics of the detected defect. The defect observables are then compared with known defect training data in order to characterize the defect as to type, depth and extent.

62 Claims, 9 Drawing Sheets

LAP
DT=15°K, $L_{c-h}$=9 Mils, D=33 Mils

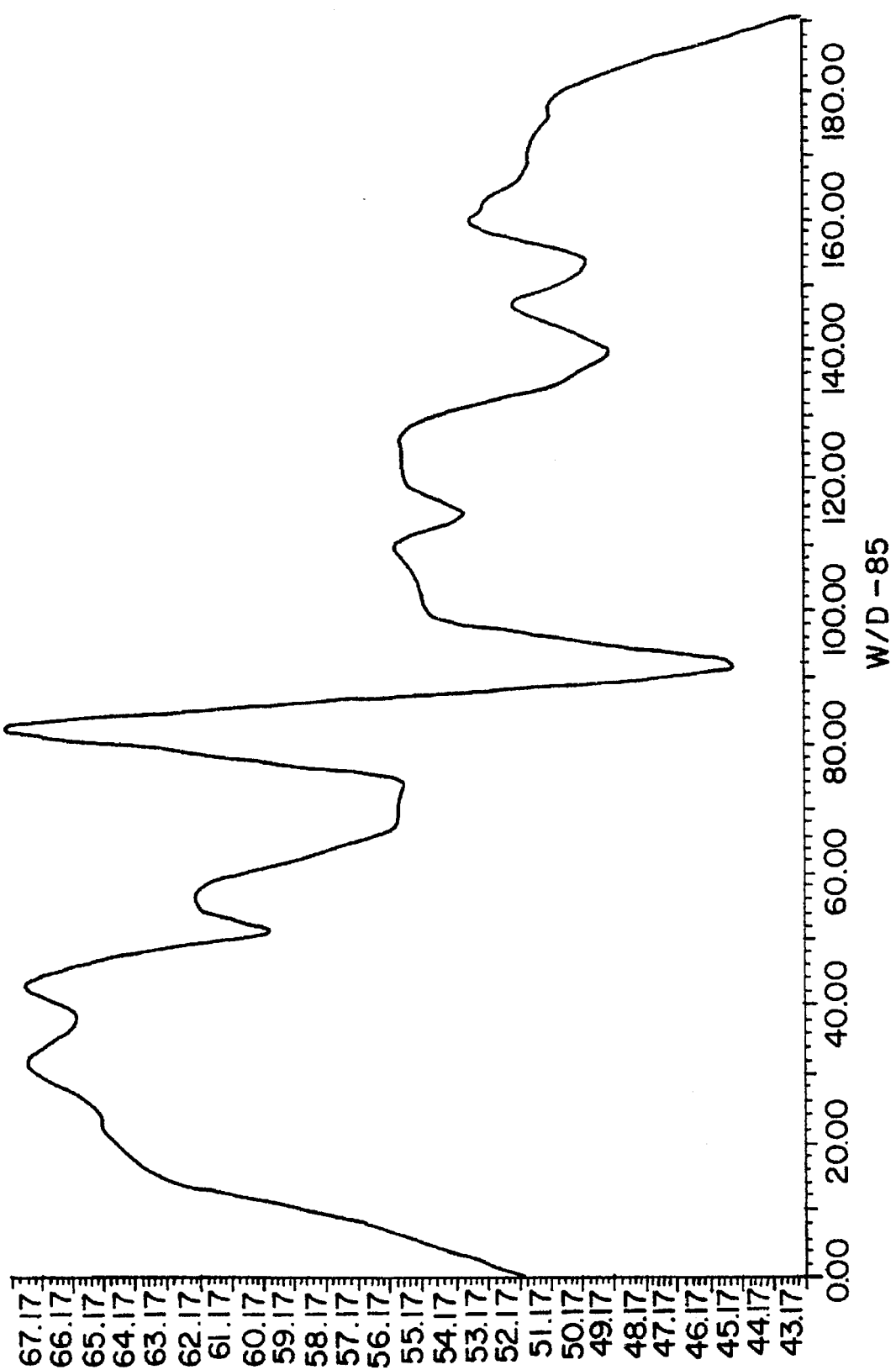

METHOD AND APPARATUS FOR REAL TIME DEFECT INSPECTION OF METAL AT ELEVATED TEMPERATURE

BACKGROUND OF THE INVENTION

The present invention relates to a system for inspecting hot, formed metal and in particular to a method and apparatus for detecting a defect in hot formed metal, or other formed material, in real time and identifying the type, depth and extent of the defect through processing IR signature data.

Steel and other metals are fashioned into various sizes and shapes such as sheets, rods, bars or wires for end user delivery. This process usually consists of heating bulk metal billets to malleable temperature and then hot-working by forging, rolling or extrusion until the desired shape and size are achieved.

Several types of defects and faults are known to occur as a result hot working of a product. Types of flaws may include cracks, laps, overfill, fins, scabs, scratches, roll marks, fire crack transfer marks, and roughness. Some flaws will have an inherently well defined structure whereas others tend to be highly unstructured to the extent of being random. Some flaw types are global, spanning the full length of the formed stock. Others are localized. Characteristic features of some flaws may be similar. This complicates the automated defect detection processes. Inspection for such flaws requires a high degree of spatial and thermal resolution.

Currently, cold inspection is generally relied upon for quality control. Cold inspection may be performed by human observation, eddy current, magnetic flux leakage, ultrasound, and/or spectroscopy techniques, for example. Such testing is complex and labor intensive due to the occasionally subtle nature of some types of flaws, an inspected material's sheer bulk mass, and the total product area which requires inspection. Typically, only random samples of worked stock can be checked. In addition, considerable time delay can occur between the time of manufacture and corresponding quality control testing. Such time delay is highly undesirable and unduly costly if inspection shows that a production adjustment is required.

Simple, low data rate on-line autonomous systems currently exist for elementary measurements such as pyrometers for temperature measurement and laser scanners or optical shadow casting for gauging. Eddy current and pyrometer based systems are being studied and used to some extent for on-line flaw inspection. However, such techniques are only marginal and ad hoc for this task since they can only sense large and repetitive product discontinuities, require special product proximity and/or handling, and generate considerable signal ambiguity requiring highly experienced human interpretation which cannot be performed in real time.

Methods that rely on reflected light cannot detect subsurface defect structure and are subject to lighting artifacts and/or blur when used for inspecting fast moving target products. Thus, TV's, CCD's, and other such visible radiation sensitive and/or slow framing cameras are unsuitable for dynamic detection of defect type and/or depth.

Examples of conventional inspection systems include U.S. Pat. No. 4,118,732 wherein a TV camera system is used to detect reflected radiant energy and determine the existence of faults or defects based on the detected differences in captured rest images. The system described is limited to surface detection and merely detects the presence of faults or defects appearing on the product surface without providing any information as to the type, depth or extent of such defects.

U.S. Pat. No. 4,319,270 also discloses a conventional video monitoring system which detects surface faults. The patent describes a method for detecting surface imperfections on the surface of a hot material. The method involves collecting video images of the surface of a material and breaking down the images into pixel signals each having a corresponding value. Average values are calculated and variously stored for later retrieval and comparison. By comparing the present pixel values with the stored averages, variations, and thus defects, are detected. Here again, however, only surface faults are detectable. Furthermore, there is no technique disclosed for determining the type, depth or extent of any of the detected faults.

U.S. Pat. No. 4,665,317 is directed to a process for sensing surface defects on a moving strip. The process involves developing an analog signal representing the image and storing the signal for processing. The signals are converted in order to assign numerical values to each signal, and then these are filtered in order to determine if a signal represents a defect. Once again, only surface faults are detectable and there is no technique disclosed for determining the type, depth or extent of any of the detected faults. The system has no real-time capability as output data is formatted for human interpretation.

U.S. Pat. No. 4,759,072 describes a method of detecting surface flaws in a hot metal body. The method involves gathering an optical video signal and a corresponding IR video signal for a given area of the surface being inspected. Each of the signals is converted into binary data and then corresponding signals are passed through a logic gate in order to determine if a defect is present. No defect type or size determination is disclosed.

Hence, it is believed that a completely satisfactory on-line automatic inspection system currently does not exist. In addition to the aforementioned problems, conventional systems fail to account and correct for translational errors brought about by vibration or translation of the inspected product and the inspection system relative to one another.

It is an objective of the present invention to provide real time on-line automatic product inspection which offers computerized analyses, minimal special material handling, 100% inspection capability, and instantaneous inspection feedback for quality control and production process control leading to reduced waste and higher efficiency. It is a further objective to provide a system which is capable of automatically compensating and correcting for movement and translational errors occurring between the inspection system and the inspected object.

Automatically quantifying metal defects, or flaws, in real time during the hot-working process benefits production process control as well as production quality control. Simply knowing in real time that a defect is being produced is good, however knowing the type of defect and its depth and/or extent is vastly superior. Identifying the defect type offers the potential for real time feedback for production control adjustment. Knowing the depth and extent of a defect in worked metal qualifies the value of the metal being produced.

In part, the inherently hostile mill environment has prevented the introduction of on-line instrumentation for automatic flaw detection and characterization. Several problems exist in inspecting a moving product in such an environment. These include the inspection of a moving product which may travel at speeds approaching several hundred miles per hour and may have significant lateral flutter (vibration). Furthermore, such product may exist at temperatures ranging up to several thousand degrees Fahrenheit. Additionally, various levels of scale buildup are typical in such environments, which scale may have flaw masking effects or may provide false designations.

Prior art systems have failed to sufficiently address and overcome such problems. None of the present, conventional systems are believed to have a capability for detecting the type of flaw in addition to its depth and extent. Most known systems rely to a great extent on the detection, differentiation and interpretation of visible spectrum light. Consequently, such systems are entirely limited to the detection of surface flaws. It is an object of the present invention to overcome these shortcomings.

SUMMARY OF THE INVENTION

The aforementioned and other objects of the invention are achieved by providing a method and apparatus having real time, on-line automatic, 100% inspection capability for quality control and process control during the actual dynamic formation of a material or metal into various shapes and sizes by hot working or other heat input. Specifically, the invention is to determine the type of defects (or "flaws") and to measure the defect depth into the metal through the infrared measurement of temperature, temperature variations, thermal lengths, and heating patterns proximal to the defect site. While the present invention is described primarily with respect to its application in metal formation systems, it will be recognized by one having ordinary skill in the art that the present invention can be applied to all types of hot material formation wherein the hot material has a substantially homogeneous thermal profile and to other types of formed materials that have a substantially homogeneous structure.

Defects in formed metal are understood to include all metal faults such as scabs, laps, scratches, grooves, fins, pits, cracks, slivers, foreign matter, roughness, etc. The present invention is believed to be novel and unique because no known prior art method and/or device has been known to accomplish, or purports to accomplish, the measurement of metal defect type and defect depth, in real time, during, or immediately following, metal manufacture by utilizing infrared sensing equipment and the accompanying processing ability.

The surface of a semi-continuous or continuous metal product in dynamic thermal equilibrium, but which is undergoing hot working, will have a substantially uniform (or slowly varying convection gradient) temperature distribution except near the ends of the metal product and at hot working contact sites. Defects can be described generically as some combination of a void, a fold, and/or an impurity which may or may not be random, and which may or may not break the surface of the metal. In any case, a defect causes a disruption of the otherwise, substantially uniform metal surface temperature.

Furthermore, oxidation of the hot metal surface may cause scale which appears to have a cooler temperature than the main metal surface. Thus scale also appears as a disruption in the otherwise uniform metal temperature and therefore might falsely be identified as a metal defect. Therefore, if scale is present, it is to be identified as such, and not regarded as a true metal defect.

Prior art systems provide only for the detection of defects and/or scale without regard to defect type or depth. The present invention represents an improvement on this art primarily in that defects are determined automatically as to the defect type and defect depth into the metal through measurement of the infrared radiation emitted from the metal.

It is emphasized that subsurface defect structure should be sensed in order to determine defect type and depth. For example, a lap running axially down a rod which is not fully closed will falsely appear as a groove or scratch to a surface sensing sensor (such as one operated with reflected light) since only the lap void is visible, the folded metal part of the lap will remain hidden.

The detection of metal flaws for the purposes of the present invention requires sensor spatial resolution on the order of a few thousandths of an inch (a few "mils", 1 mil=0.001") and thermal resolution on the order of a few °F. For products at temperatures only slightly above room temperature, inadequate signal energy is emitted for defect detection below the mid infrared (IR) spectral region (approximately 3 to 14 microns) for high resolution measurements. Thus, to achieve the high spatial and thermal resolution required for the measurement of defect type and depth based on the emitted heat pattern—in spite of any high speed product motion or low product temperature—the data acquisition system should operate in a snapshot mode and detect mid infrared radiation. A defect heat pattern or signature is formed from heat being either transmitted through or shunted around the defects thus casting a "thermal shadow" on the metal surface which can be sensed in infrared and analyzed to determine the depth, extent and type of the defect.

The present invention has several significant advantages over the prior art. The prior art does not determine metal defect depth or defect type automatically in real time using infrared detection. A system for automatically determining defect type and depth in real time has not been accomplished by any other known technique.

The invention provides a means to acquire and process infrared data from a fast translating/vibrating product through the use of a product constraint, or guide (if needed), which maintains the moving product within a camera lens focal region. Typically, stop action (fast framing) infrared cameras are used, and full product sensing can be achieved by use of multiple cameras situated about a moving product.

Features of the present invention include: the combined employment of guides/constraints, infrared cameras/lenses, real time processors, and computers to acquire and process infrared data from metal products for the determination of metal defect type and defect depth. The metal should be at an elevated temperature.

In general, the system operates by scanning infrared emissions radiating from a selected area of a formed piece of metal. The scan is first processed in a lateral or transverse direction, and then the transverse scans are compiled in a contiguous linear direction along the direction of scanning or product movement (typically a lengthwise or longitudinal direction). The process involves detecting the temperature of the scanned portions of the formed product and maintaining a running average for the temperature. Scan data is typically converted into pixel data. During processing of a particular transverse scan, heating maxima and minima are determined relative to the running average. Deviations from the average may indicate the presence of a defect, and the extent of the deviation may be used to determine the depth of a defect. Contiguous sequential transverse scans are collected and aligned to compensate for flutter and/or vibration. The contiguous scans are used for longitudinal processing of the scan data. This is accomplished by associating a transverse scan data line with that of a next and/or previous transverse scan data line. If a defect is detected in a first scan, tracking is initiated in order to trace the defect in subsequent scans.

From the tracking data, the defect size, shape, and type can be determined. This is done by measuring and comparing the pixels which represent defect location data between the tracked scans in order to trace the defect and compile relevant data regarding the defects particular characteristics. Defect identification involves comparing a particular tracked defect signature and characteristics with that of known defect signature and character data which has previously been stored in the system. The system may also be capable of entering a learning mode in order to store first impression defect data.

The invention involves an apparatus for scanning an object in order to determine the extent and type of a defect which may appear within the object. The apparatus includes an IR detection device directed at a focal region on the object for detecting IR radiation emitted at the focal region and outputting corresponding detection signals for the focal region including a temperature reading. Also provided is a device for advancing the focal region relative to the object to a next contiguous focal region, and calculating means for maintaining a running average of detected temperatures and calculating a deviation threshold corresponding to the running average. A memory is provided which contains known defect profiles. Defect existence is determined when a detected temperature exceeds the deviation threshold. Defect depth is determined by a assessing the gradient of temperature difference between detection signals for a particular focal region. Defect types are identified by opening a tracking file when a defect is first detected and tracking the defect through contiguous focal regions to generate a defect signature and comparing the signature with the known defect profiles. The computing or calculating means may include a data processing means which handles the data collected by the detector. Such a data processing means may involve a transverse data processing means for processing data corresponding to a particular focal region. A longitudinal data processing means may be provided in order to compile and correlate contiguous transverse scan data.

The invention also involves a method for scanning an object in order to determine the extent and type of defect present in the object, which method involves the steps of detecting IR radiation emitted at a focal region and outputting corresponding detection signals for the focal region including a temperature reading; adjusting either the object, the IR detector or a lens for the IR detector in order to advance the focal region relative to the object to a next contiguous focal region; maintaining a running average of detected temperatures and calculating a deviation threshold corresponding to the running average; detecting a defect when a detected temperature exceeds the deviation threshold; determining the defect depth by assessing the temperature gradient between detection signals for a particular focal region; identifying the defect type by opening a tracking file when a defect is first detected and tracking the defect through contiguous focal regions to generate a defect signature and comparing the signature with known defect profiles stored in memory. The method also may involve generating transverse scan data corresponding to a detected signal and compiling and correlating such transverse scan data.

The invention may be applied to all types of cast, rolled, extruded, or forged shapes such as round, square, rectangular, hexagonal, etc. The invention may also be applied to pipe and wire inspection as well as to inspection of angle and channel shaped metal.

The invention may be applied to inspection of moving sheet steel by positioning sensors so that their combined field of view forms a "curtain" through which the sheet steel passes upon inspection or by optically scanning a linear focal plane array across the sheet.

The system may operate by passing formed metal through the focal area of a stationary sensor or sensors, moving sensors relative to a stationary object to be inspected, or by using a movable focal device to collect an object's IR emissions and direct them to a sensor.

The invention may also be applied to static metal inspection by optically scanning linear focal plane array cameras or by replacing the linear focal plane array cameras with two dimensional imaging infrared cameras. The IR camera could be positioned over the metal or moved slowly, with processing being basically the same as described above.

In order to advance the focal region of the inspection device relative to the inspected object, inspection may involve actively scanning, self scanning, or a hybrid technique of the former and latter. Active scanning may involve a mechanism (e.g., a mirror) to sweep the field of view (FOV) over a particular object focal region. Self scanning would not involve articulating optics, but rather a fixed optical system, wherein the object would be passed through the detector's FOV. A fixed detector is envisioned for a system wherein a rod, bar or wire is hot rolled or extruded, and then passed through the inspection system detector shortly after working. In a system for inspection plates, sheets or other discrete objects, a hybrid system is contemplated where a directable optic is employed whose FOV is swept over an object which is moving.

Other objects and advantages of the invention will become readily apparent from the drawings and detail description set out below.

BRIEF DESCRIPTION OF THE DRAWINGS

FIG. 8 depicts a transverse defect signature of the lap defect shown in FIG. 7.

DETAILED DESCRIPTION OF THE PREFERRED EMBODIMENTS

Figure 1:
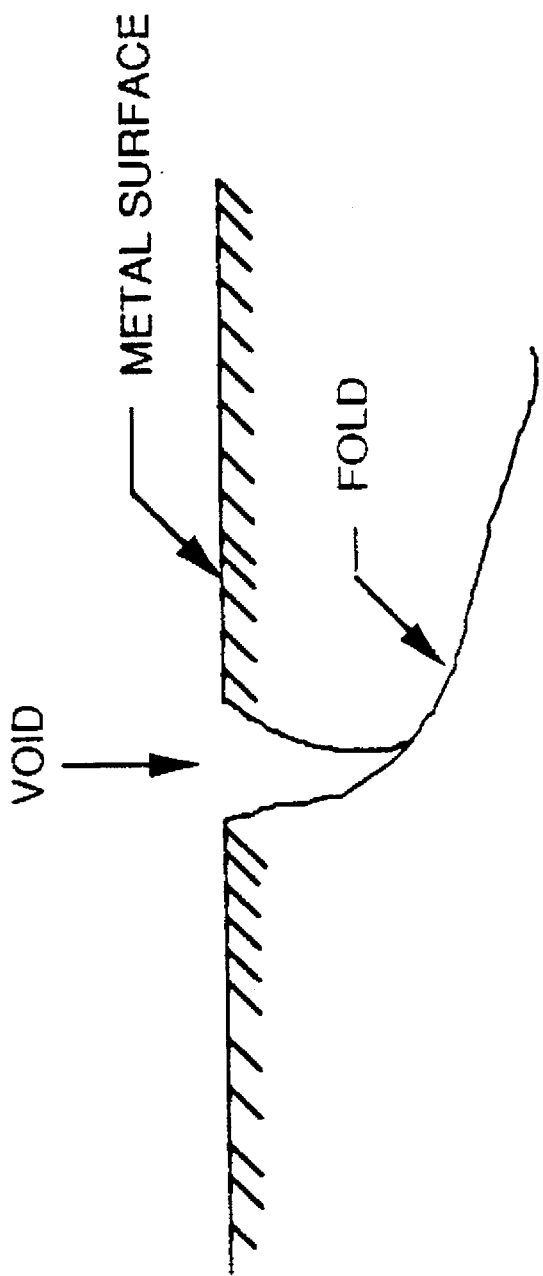
FIG. 1 depicts a cross section of a lap defect consisting of a void and fold combination.
Figure 2:
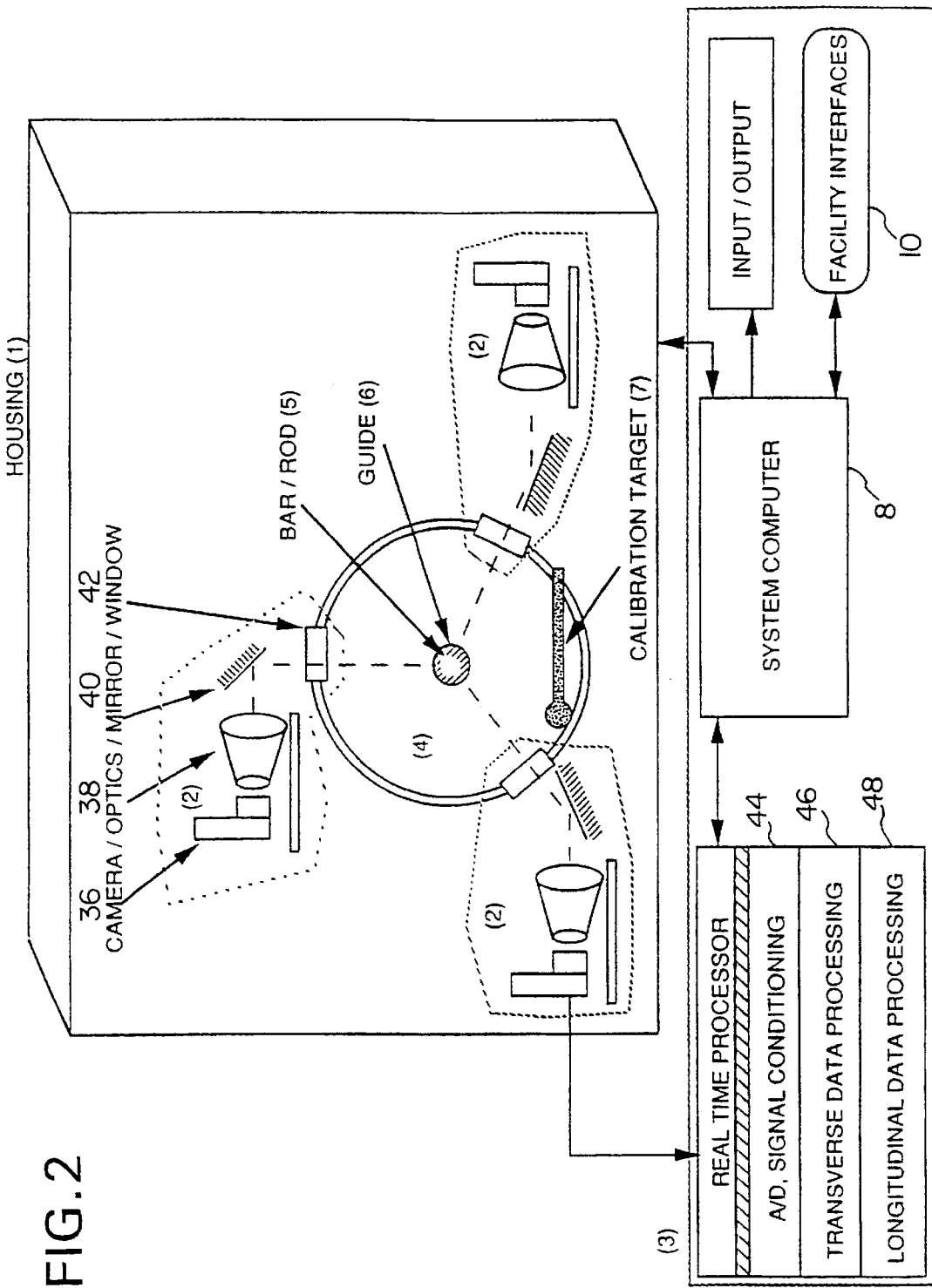
FIG. 2 depicts a bar and rod inspection system corresponding to an embodiment of the present invention.

Turning now to the figures, FIG. 2 depicts an exemplary application of the present invention wherein a housing 1 with several infrared (IR) detector cameras 2 surrounding a moving product 5. A data processing/display unit 3 also is depicted. The housing serves as a platform for the infrared cameras 2 which may be situated around a central opening in the housing 4. A subject rod or bar 5 to be inspected may be confined to move through the approximate center of the housing central opening 4 by a guide 6. Several IR cameras 2 are typically arranged about the housing central opening 4 and view the rod or bar 5 at an angle perpendicular to the rod or bar's direction of motion. Such an arrangement is typically located close to an extrusion port, or the equivalent, where a bar, rod or wire will have an appropriate temperature and where defects can be quickly detected in order to provide appropriate feedback to production systems.

A heated calibration target 7 may be provided allowing the IR cameras 2 to be calibrated (preferably in software) when viewing the calibration target 7 whose temperature is known. IR detector calibration may be performed prior to use for rod and bar inspection. When used, the calibration target 7 may be moved to the center of the opening for calibration viewing by the sensors. Alternatively, the IR cameras 2 may be trained on a fixed calibration target. Use of a calibration target may also allow for diagnostics such as identification of dead pixels and/or window transmission problems. Secondarily, use of a calibration target having a known temperature allows for system calibration for measurement of the rod/bar temperature by way of a look up table which contains relevant calibration information, such as emissivity, for a particular type of metal or material being inspected.

Each IR detector camera 2 may consist of a linear (single or multiple row) detector focal plane array (such as the Cincinnati Electronics Corp. InSb IHL series) oriented perpendicular to the motion of the bar/rod. Each camera 36 may be fronted by an IR lens optical system 38 which brings the product into focus at the detector array. A mirror 40 may be used to reflect IR radiation emitted by bar/rod 5 toward the camera/optics arrangement 36/38. Such IR radiation may pass through a window 42 in the central opening 4.

The bar or rod's motion transverse to its length and direction of travel in the system (called flutter) preferably is confined sufficiently by the guide 6 so that the bar or rod remains within the camera/optical system's field of view and depth of field.

Spatial resolution depends upon the overall transfer function of the optics, camera, and electronics of the defect detection system. However, along the rod/bar direction of motion, the spatial resolution may also depend upon the dwell time of the camera due to the motion. The relative motion of the rod/bar during a camera dwell period may be more or less than a pixel size and will, in general, result in an averaging effect along the rod/bar. Dwell times should be selected to be equal to or less than the time it takes the target to traverse a distance equal to the pixel size to obtain a maximally resolved "snapshot" image of the target (alternatively, a two dimensional IR camera may be used provided a snapshot mode is available—such as the Lockheed Santa Barbara Focal Plane ImagIR). The camera read out need not be synchronized to the speed of the rod/bar.

The camera system's spatial and thermal resolution should be sufficiently refined in order to satisfy whatever the desired ultimate resolution/sensitivity requirements are for a particular object being inspected to allow for measurement of the defect type and depth. Spatial and thermal resolution factors may depend on the minimum defect size and maximum rod/bar speed. The required spatial resolution is generally on the order of mils (thousandths of an inch) while thermal resolution is on the order of a few degrees Fahrenheit for product velocities of up to several hundred feet per second.

Figure 3:
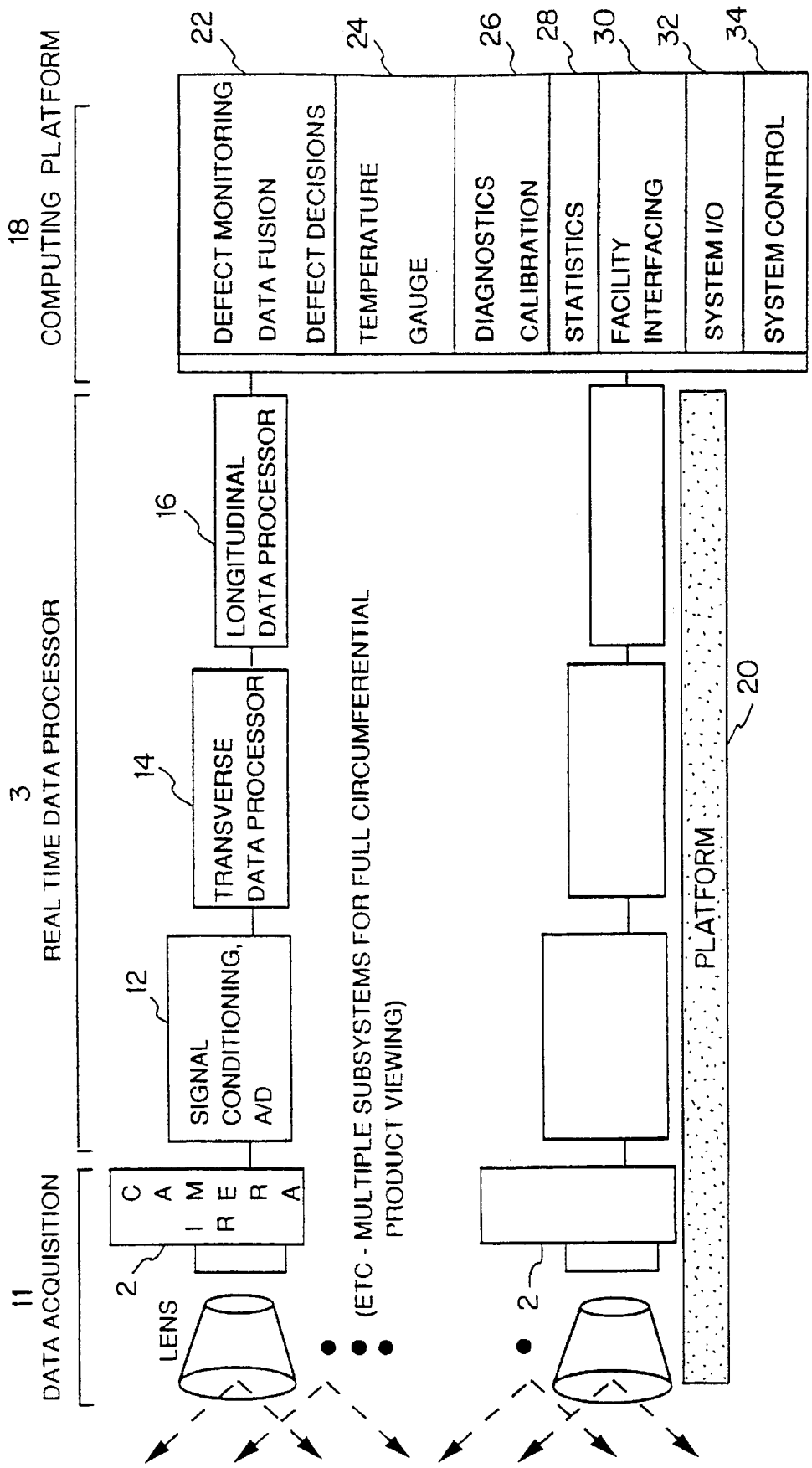
FIG. 3 depicts a defect inspection system diagram.

At the completion of a camera's dwell time, the sampled data collected by the IR detector array is read out by drive electronics, amplified, conditioned and converted to digital data, and then processed as "transverse data" and subsequently as "longitudinal data" in real time. The data is typically fed to a real time processor 3 or a comparable software computing system. A diagram for an exemplary system for handling and processing the data is depicted in FIG. 3.

A transverse data string (transverse column of data across the rod/bar) will be referred to as a "scan" or "scan line." A transverse scan is comprised of detector data taken from a region of the rod or bar which is perpendicular to the longitudinal axis of the rod or bar. In an application wherein a planar object is being inspected, the transverse scan may be perpendicular to the direction of relative movement between the IR detector and the inspected object. Sequential transverse scans can be composed into an apparent image of the rod/bar for each camera view. If the camera readout is not synchronized with the target motion, the image of the product may be compressed or expanded in scale.

Figure 4:
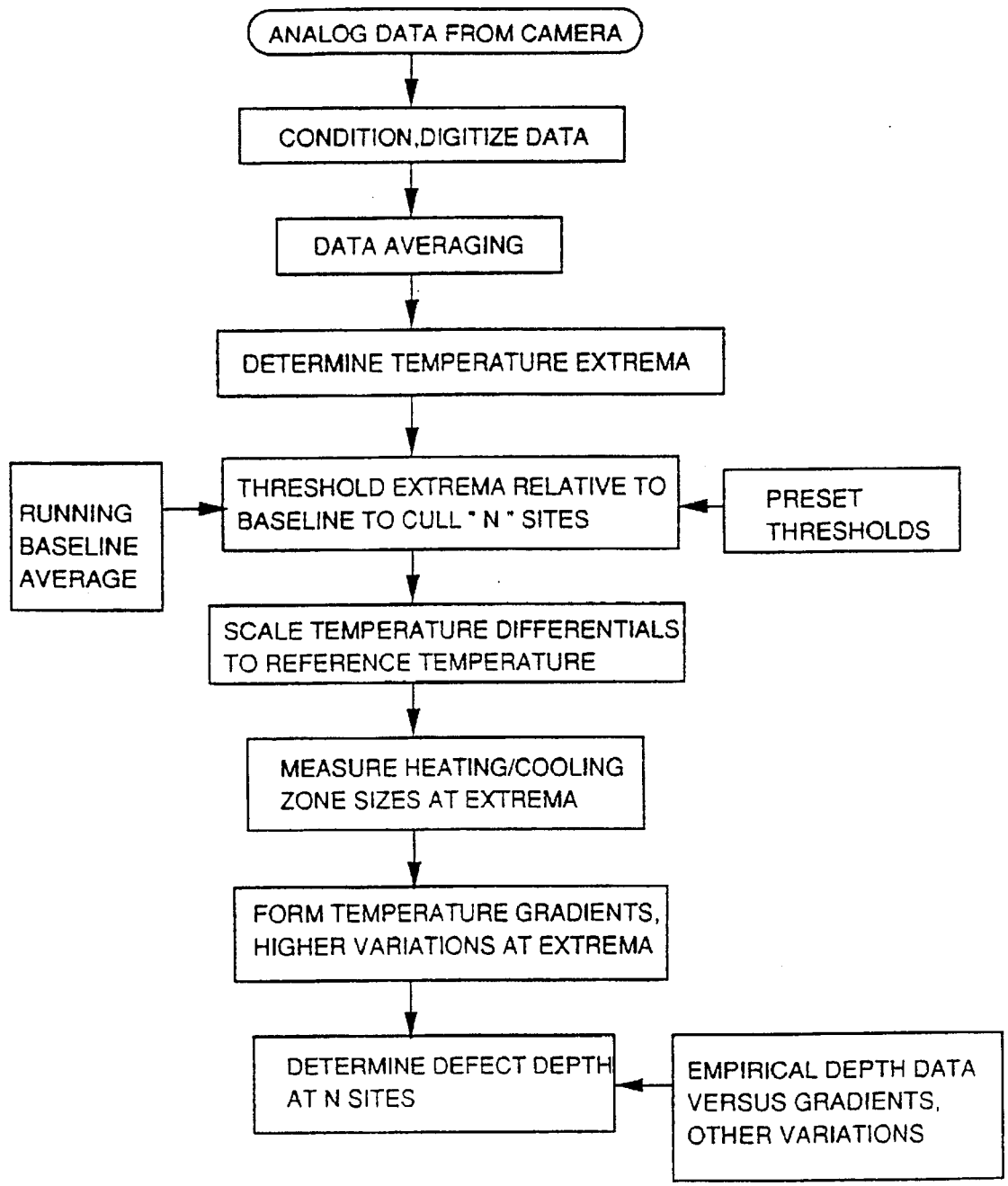
FIG. 4 is a flowchart depicting transverse data processing.

Transverse real time data processing 46 is done at high data rate and may be done with wired logic (such as field programmable gate array (FPGA) logic), with a massively parallel computer system, or any other appropriate system in order to achieve a desired result. Transverse data processing steps are shown in the flow diagram depicted in FIG. 4. The data is first preamplified, conditioned, and digitized. It is then minimally averaged to reduce noise. The highest heating maxima and cooling minima are determined across the scan data which maxima and minima are beyond a preset threshold level calculated relative to a running baseline average (baseline temperature) of the thermal IR data. A defect free object will have a homogeneous apparent thermal signature (temperature profile), however, it may possibly have a thermal gradient due to convection. Defects may appear as deviations from such temperature homogeneity across and along the rod/bar. Defect presence is detected by the measurement of a temperature variation (differential change from the baseline average temperature) beyond the preset threshold. Since defect temperature variations depend on the nominal rod/bar average temperature, measured temperature differentials must be scaled to a fixed (reference) temperature for comparison purposes. At the thermal maxima and minima (extrema) sites, the differential thermal heating/cooling temperatures are determined as well as the pixel width about the heating and cooling extrema sites. From this data, average first derivatives of defect thermal signatures may be formed from the temperature and length differentials. These thermal differentials allow determination of maximum depth through empirically derived relationships and correlations. These relationships are established, for example, from training data based upon voids and folds of known dimensions or other known defect characteristics.

A void in hot metal acts as a cavity producing an apparent heating effect with slight cooling in adjacent regions. A fold in hot metal produces an apparent cooling effect over the folded metal with heating in adjacent regions. Once thermal IR data is obtained on such training samples, the data may be sectioned to measure the maximum defect depth. The maximum depth of the void/fold is then related (correlated) through such empirical data to the average void/fold temperature gradient (first derivative) as determined above. This correlation is determined empirically and generally depends on the type of defect and on the nature of the rod/bar material properties. The temperature gradient for a fold tends to be a nearly monotonically increasing linear relationship with maximum fold depth whereas that for a void tends to be a nearly monotonically decreasing inverse linear relationship with void depth. The latter relationship is depicted in FIG.

5. Thus, defect depth is measured by correlating the defect temperature variation across the defect and the defect's corresponding apparent thermal width (both of which are readily measurable) to the defect depth which is determined by actual sectioning (cutting of the metal, mounting, and microscopic measurement).

Fundamentally, to first order, the defect temperature differential in dynamic equilibrium is related to the defect mass density, volume, and specific heat. Thus follows the correlation between defect temperature differentials and defect volumetric parameters. Refinements on the defect depth structure, including maximum depth measurement, can be accomplished using second and higher order thermal derivatives.

Figure 6:
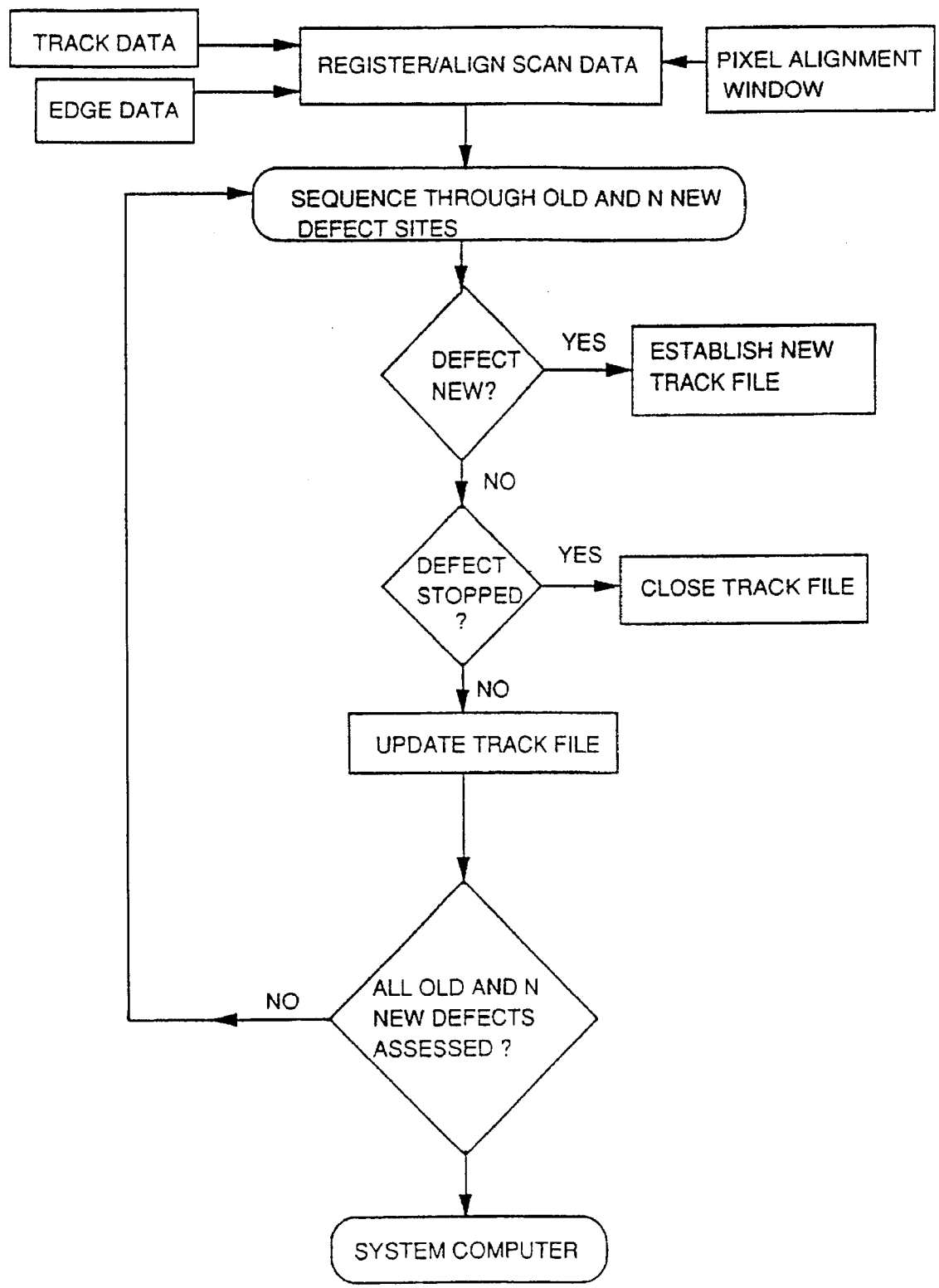
FIG. 6 is a flowchart depicting longitudinal data processing.

Longitudinal real time data processing 48 consists primarily of creating and maintaining defect track files as shown in FIG. 6 for the purpose of defect classification. Due to product flutter, subsequent scan lines should be registered (spatially aligned pixel by pixel with a previous transverse scan) in order to associate any propagation of a defect along the direction of product velocity. A registration is made to align the defects into defect track files to account for defect propagation along the product velocity direction. To accomplish this, defects on traverse scan lines are associated with those on subsequent traverse scan lines provided the defects on the subsequent scan lines align within a "window" which may be several pixels wide depending on the size of the detected defect. When the location of a product edge is known, it may be used as a reference for registration. Scan to scan data association (that is, defect "tracking") is performed from one registered scan line to the next (the apparent rod/bar IR image) as the rod/bar moves by, so that the extent (length) of the defect along the rod/bar can be measured, and also so that the defect type can be determined through the two dimensional heating pattern of the defect in the object surface. By tracking the defect and effectively mapping its dimensions pixel by pixel, a signature of the defect is generated. Utilizing known rod/bar speeds obtained, for example, from a tachometer, combined with timing obtained from a system clock, defect location is readily determined relative to the end(s) of the rod/bar or a known location.

Defects cannot be fully characterized as to type and greatest depth until the longitudinal defect track file data are established which are synthesized of the transverse data. A true correlation transform between a known reference defect filter and the unknown defect cannot, in general, be reliably carried out for classification and/or recognition purposes since defects tend to be highly randomized and since varying image scale compressions are likely. Thus, for purposes of determining defect type relating to each track file, the heating pattern characteristic features of known defect types are stored in the system in advance. Defect identification of a track file is established through a logical comparison between the characteristic pattern features of the track file generated for a detected defect and the pattern features relating to known defect types stored in the system. Defect pattern features include characteristic spatial, thermal, and radiometric averages and moments as well as qualitative pattern features such as heating/cooling and shape/size relationships across and along the defect. Defect analyses and assessments are performed at the system computer level and may be performed on a system such as that depicted in FIG. 3. The system is also capable of entering a learn mode for capturing characteristics and profiles for previously unencountered defect types. Scale is distinguished from true defects due to its characteristics of having an extremely abrupt cooling gradient and extreme randomness of appearance.

A typical system for carrying out the afore-described process is depicted in FIG. 3. Such a system includes a data acquisition portion 11 comprised of appropriate IR detectors and/or cameras, a real time processing section 3 for signal handling, and a computing platform, processing circuitry, or workstation 18 for analyzing the data. As previously discussed, the data acquisition portion 11 can be comprised of any appropriate IR detector(s), associated mirrors, lenses, or signal transmission devices to collect the object's IR emissions for transmission of the appropriate information to the real time data processor 3. The data processor 3 may be any device or system selected to achieve a desired signal handling result in real time. Such a system may be provided by a hard wired circuit, programmable logic/gate array, microprocessor, digital signal processor, or by real time parallel processing in software or firmware. A workstation, personal computer or other appropriate computing system or platform may be used to perform appropriate analysis of the collected and processed data. Such a system may be appropriately selected in order to accomplish a desired result. Analysis and output functions handled by the computing platform 18 involve defect monitoring, data fusion and defect decision analysis 22; metal temperature and gauging measurement 24; diagnostics and calibration 26; statistical analysis 28; facility interfacing 30; system input/output 32; and system control 34.

Figure 5:
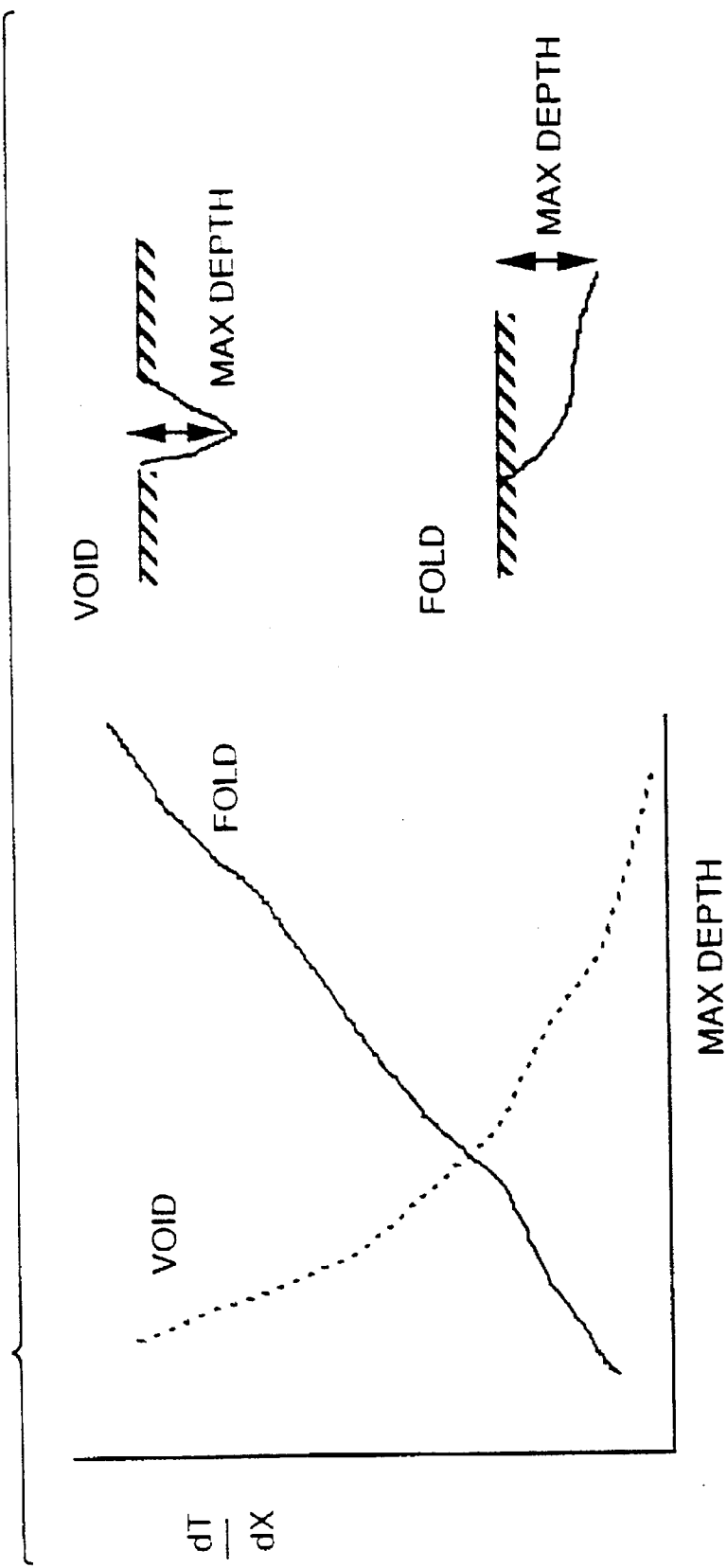
FIG. 5 depicts a temperature gradient correlation data for a void defect and a fold defect.
Figure 7B:
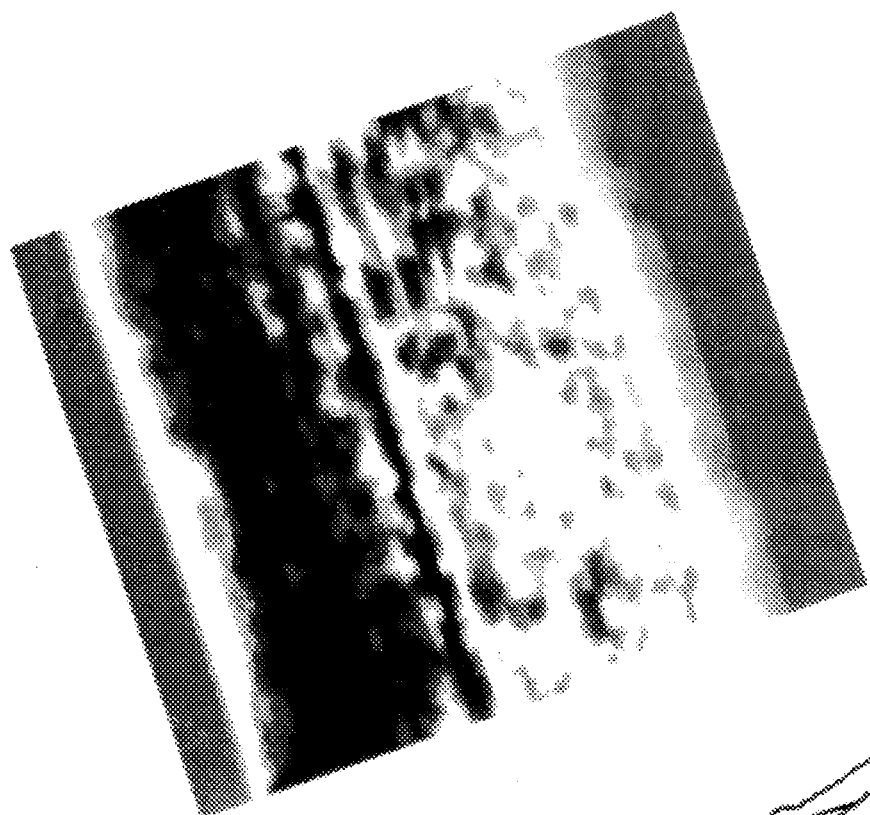
FIG. 7 shows a depiction of an analog infra red image of a typical lap defect and corresponding digitized images of transverse scans of the lap defect.
Figure 7A:
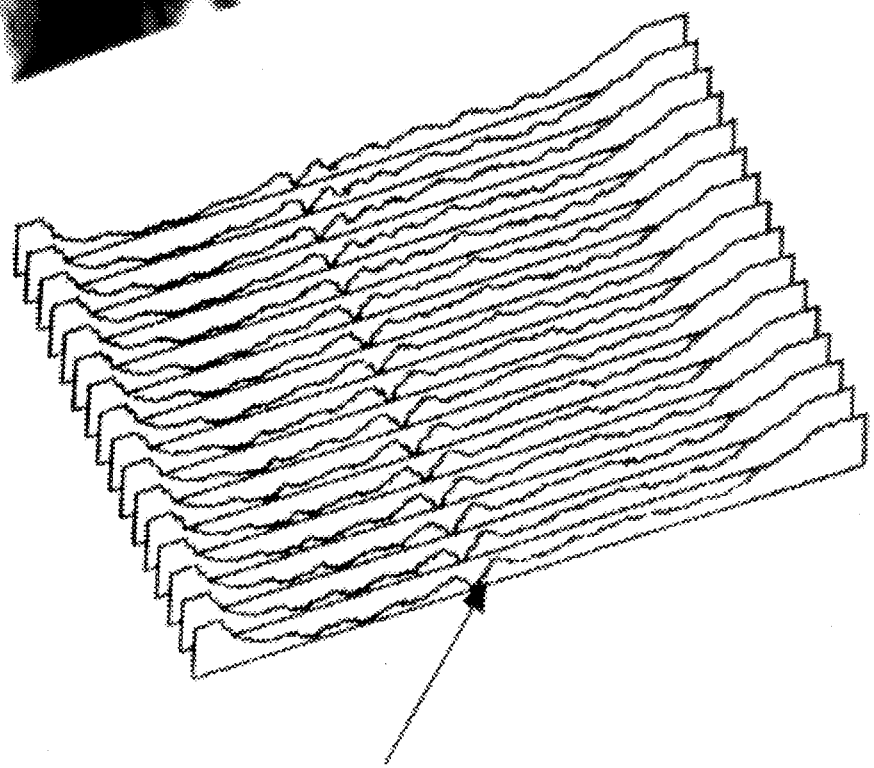
Figure 9:
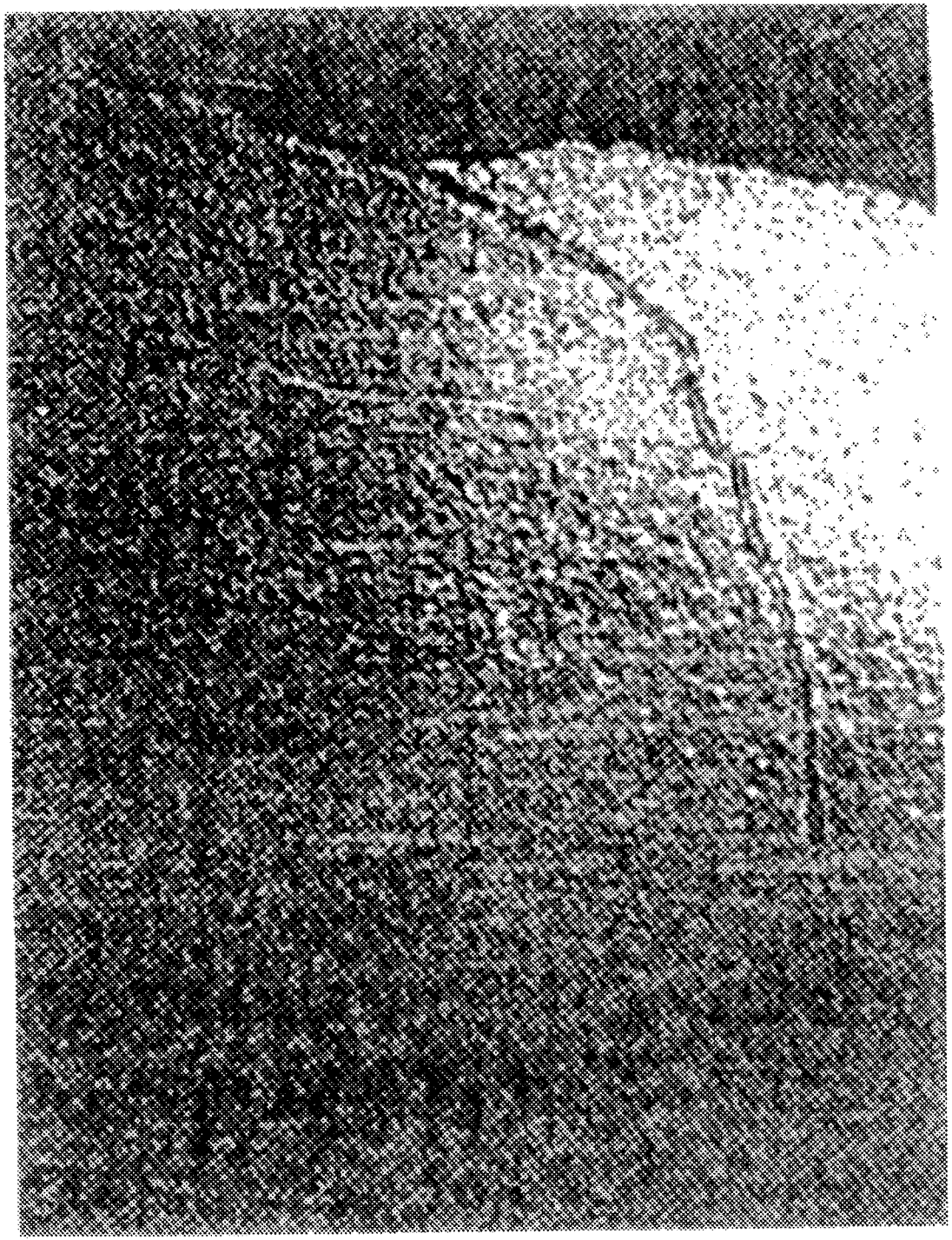
FIG. 9 is a depiction taken from a photomicrograph of a cross section of the object shown in FIG. 7 depicting the lap defect.

Typical infrared and metric data for a lap defect are shown in FIGS. 7, 8 and 9. The illustration of a steel rod cross section shown in FIG. 9 depicts a magnified lap defect. Also shown in FIG. 7 are an illustration corresponding to an 8 to 12 micron infrared analog image and digital signature scan data for the lap which have been assembled into images. A single "scan" line is shown in FIG. 8. It is seen that very characteristic heating and cooling (y—axis related to temperature) effects are measured versus position across (x—axis) and along (adjacent scan lines) the defect. Training consists of associating just such infrared and metric data on defect type and depth as shown in FIG. 5.

Enhanced confidence and measurement accuracy are obtained through sensor fusion analysis techniques on defects which are viewed simultaneously by multiple cameras from different aspects. Such overlapping may be seen in the arrangement depicted in FIG. 3. A defect pattern which is viewed by two cameras from different aspects will appear similar but with metric foreshortening. Temperature differentials will also differ between the two cameras due to the effect commonly known as Lambert's Law. Such defect correlation from camera-to-camera may enhance defect detection and identification processes. Such association, data fusion, and comparisons/analysis may be made at the system computer level as indicated in FIG. 3.

One having ordinary skill in the art will appreciate that the afore-described system can be utilized to detect and identify defects in any formed product which has a substantially uniform temperature profile (other than ordinary attendant noise and natural or forced convection gradients) wherein flaws may be revealed by a departure from an otherwise homogeneous heat signature. Any suitable IR detector(s) capable of gathering appropriate IR signals may be utilized. Once acquired, the signals may be processed into transverse and lateral data using appropriate real time hardware processors, programmable gate/logic arrays, or parallel processing systems. Any computing system capable of analyzing the processed IR data in real time will be sufficient. It will further be recognized by one having ordinary skill in the art that the invention is not limited to the exemplary application described above. The invention can be practiced by utilizing a movable scanning or inspection device in order to detect defects in a stationary object. Furthermore, a directable lens system may be used to advance the data acquisition focal region along an object.

Although the invention has been described and depicted with respect to FIGS. 1 through 9, those skilled in the art will appreciate and understand that several variations beyond those described may be made without departing from the scope and spirit of the present invention as claimed below.

What is claimed is:

1. An apparatus for inspecting an object in real time to determine an existence of a defect in the object, said apparatus comprising:

an IR detection device directed at a focal region on the object in order to detect IR radiation emitted from the focal region, said detection device outputting detection signals corresponding to the focal region which signals include temperature;

a means for advancing the object to inspect another contiguous focal region on the object;

computing means for maintaining a running average of detected temperatures and calculating a deviation threshold corresponding to said running average; and a memory containing pre-stored known defect profiles;

said computing means determines the existence of the defect when a detected temperature exceeds said deviation threshold;

said computing means determines a defect depth when the defect exists by analysis of a temperature gradient between detection signals in a particular focal region;

said computing means determines a defect type by tracking the defect after the defect is detected and mapping the existence of the defect through contiguous focal regions to generate a defect signature pattern and comparing the signature with said pre-stored known defect profiles.

2. An apparatus as claimed in claim 1 wherein, said IR detection device is an IR camera having at least one linear focal plane array.

3. An apparatus as claimed in claim 1 wherein, said means for advancing the focal region relative to the object is a system which forms the focal regions prior to inspection of said object.

4. An apparatus as claimed in claim 1 wherein, said means for advancing the focal region relative to said object is an arrangement for moving said IR detection device over an object to be inspected which object is stationary.

5. An apparatus as claimed in claim 1 wherein, said means for advancing the focal region relative to the object is a movable optic arrangement which is capable of directing IR radiation.

6. An apparatus as claimed in claim 1 wherein, said computing means includes a computer which utilizes parallel processing.

7. An apparatus as claimed in claim 1 wherein, said computing means includes a programmable gate array.

8. An apparatus as claimed in claim 1 wherein, said computing means further includes an analog to digital converter.

9. An apparatus as claimed in claim 1 wherein, the object is formed metal having a temperature higher than an ambient temperature.

10. An apparatus as claimed in claim 1 wherein, a plurality of IR detection devices are utilized in order to provide enhanced inspection of the object.

11. An apparatus as claimed in claim 10 wherein, said IR detection devices are arranged in order to inspect an entire perimeter of the object.

12. An apparatus as claimed in claim 1 wherein, said IR detection device further detects spatial characteristics of the object.

13. An apparatus as claimed in claim 1 wherein, a shape of the object is selected from a group consisting of a bar, a beam, a rod, a wire, a sheet, and a plate.

14. An apparatus as claimed in claim 1 wherein, said apparatus further includes a calibration element.

15. An apparatus as claimed in claim 1 wherein, said apparatus further includes a guide for maintaining said object proximal to a focal area of said IR detection device.

16. An apparatus as claimed in claim 1 wherein, said IR detection device includes a mirror and optics for directing said IR radiation.

17. An apparatus for inspecting an object in real time to determine an existence of a defect in the object, said apparatus comprising:

an IR detection device directed at a focal region on the object in order to detect IR radiation emitted from the focal region, said detection device outputting detection signals corresponding to the focal region which signals include temperature;

a means for advancing the object to inspect another contiguous focal region on the object;

transverse data processing means for processing detection signals from said focal region and generating transverse scan data corresponding to said focal region:

longitudinal data processing means for compiling and correlating contiguous transverse scan data to generate an object profile;

computing means having a memory for comparing said object profile with know defect profiles stored in said memory.

18. An apparatus as claimed in claim 17 wherein, said IR detection device is an IR camera having at least one linear focal plane array.

19. An apparatus as claimed in claim 17 wherein, said means for advancing the focal region relative to the object is a system which forms the focal regions prior to inspection of said object.

20. An apparatus as claimed in claim 17 wherein, said means for advancing the focal region relative to said object is a system for moving the IR detection device over the object to be inspected which object is stationary.

21. An apparatus as claimed in claim 17 wherein, said device for advancing the focal region relative to the object is a movable optic arrangement which is capable of directing IR radiation.

22. An apparatus as claimed in claim 17 wherein, said transverse and said longitudinal data processing means include a computer which utilizes parallel processing.

23. An apparatus as claimed in claim 17 wherein, said transverse and said longitudinal data processing means include a programmable gate array.

24. An apparatus as claimed in claim 17 wherein, said computing means further includes an analog to digital convertor.

25. An apparatus as claimed in claim 17 wherein, said computing means is a computer.

26. An apparatus as claimed in claim 17 wherein, the object is formed metal having a temperature higher than an ambient temperature.

27. An apparatus as claimed in claim 26 wherein, a shape of the object is selected from the group consisting of a bar, a beam, a rod, a wire, a sheet and a plate.

28. An apparatus as claimed in claim 17 wherein, a plurality of IR detection devices are utilized in order to provide enhanced inspection of the object.

29. An apparatus as claimed in claim 28 wherein, said IR detection devices are arranged in order to inspect an entire perimeter of said object.

30. An apparatus as claimed in claim 17 wherein, said IR detection device further detects spatial characteristics of the object.

31. An apparatus as claimed in claim 17 wherein, said apparatus further includes a calibration element.

32. An apparatus as claimed in claim 17 wherein, said apparatus further includes a guide for maintaining the object within a focal area of the IR detector.

33. An apparatus as claimed in claim 17 wherein, said IR detection device includes a mirror and optics for directing said IR radiation.

34. An apparatus for inspecting an object in real time to determine an existence of a defect in the object, said apparatus comprising:

an IR detection device directed at a focal region on the object in order to detect IR radiation emitted from the focal region, said detection device outputting detection signals corresponding to the focal region which signals include temperature;

a means for advancing the object to inspect another contiguous focal region on the object;

data processing means for processing detection signals from contiguous focal regions into an object profile;

computing means having a memory for comparing said object profile with defect profiles stored in said memory.

35. An apparatus as claimed in claim 34 wherein, said IR detection device is an IR camera having at least one linear focal plane array.

36. An apparatus as claimed in claim 34 wherein, said device for advancing the focal region relative to the object is a system which forms the focal regions prior to inspection of the object.

37. An apparatus as claimed in claim 34 wherein, said device for advancing the focal region relative to the object is a system for moving said IR detection device over the object to be inspected which object is stationary.

38. A apparatus as claimed in claim 34 wherein, said device for advancing the focal region relative to the object is a movable optic arrangement which is capable of directing IR radiation.

39. An apparatus as claimed in claim 34 wherein, said data processing means includes a computer which utilizes parallel processing.

40. An apparatus as claimed in claim 34 wherein, said data processing means includes a programmable gate array.

41. An apparatus as claimed in claim 34 wherein, said computing means further includes an analog to digital converter.

42. An apparatus as claimed in claim 34 wherein, said computing means includes a computer.

43. An apparatus as claimed in claim 34 wherein, the object is formed metal having a temperature higher than an ambient temperature.

44. An apparatus as claimed in claim 43 wherein, a shape of the object is selected from the group consisting of a bar, a beam, a rod, a wire, a sheet and a plate.

45. An apparatus as claimed in claim 34 wherein, a plurality of IR detection devices are utilized in order to provide enhanced inspection of the object.

46. An apparatus as claimed in claim 45 wherein, said IR detection devices are arranged in order to inspect an entire perimeter of the object.

47. An apparatus as claimed in claim 34 wherein, said IR detection device further detects spatial characteristics of the object.

48. An apparatus as claimed in claim 34 wherein, said apparatus further includes a calibration element.

49. An apparatus as claimed in claim 34 wherein, said apparatus further includes a guide for maintaining the object proximal to a focal area of said IR detector.

50. An apparatus as claimed in claim 34 wherein, said IR detection device includes a mirror and optics for directing said IR radiation.

51. A method for inspecting an object in real time to determine an existence of a defect in the object, said method comprising the steps of:

detecting IR radiation emitted by the object at a focal region;

outputting detection signals corresponding to said focal region which detection signals include temperature;

advancing said focal region relative to the object to the next contiguous focal region;

maintaining a running average of detected temperatures and calculating a deviation threshold corresponding to said running average;

indicating defect detection when a detected temperature exceeds said deviation threshold;

determining a defect depth by assessing temperature gradient between detection signals for a particular focal region;

identifying a defect by opening a tracking file when the defect is detected and mapping the defect through contiguous focal regions to generate a defect signature and comparing said defect signature with known defect profiles stored in memory.

52. A method as claimed in claim 51 wherein, said method further includes converting said detection signals into digital transverse scan data.

53. A method as claimed in claim 52 wherein, said method further involves spatially aligning consecutive transverse scan data in a direction of relative motion between an IR detector and the object.

54. A method as claimed in claim 51 wherein, said method further includes determining an extent of the defect by measuring a number and arrangement of pixels which make up said defect signature.

55. A method as claimed in claim 52 wherein, said method further comprises:

opening the tracking file when a defect is detected; and mapping the defect in subsequent transverse scan data.

56. A method as claimed in claim 51 wherein, said method further comprises:

entering a learning mode when a particular detected defect fails to match known defect profiles stored in memory; and storing characteristics of the particular detected defect in memory.

57. A method as claimed in claim 51 wherein, said method further comprises:

performing noise reduction on said detected signals.

58. A method for inspecting an object in real time to determine an existence of a defect in the object, said method comprising the steps of:

detecting IR radiation emitted by the object at a focal region;

outputting detection signals corresponding to said focal region which detection signals include temperature;

generating transverse scan data by converting said detection signals into digital data;

advancing said focal region relative to the object to a next contiguous focal region;

compiling and correlating contiguous transverse scan data in order to generate an object signature;

maintaining a running average of detected temperatures and calculating a deviation threshold corresponding to said running average;

indicating defect detection when a detected temperature exceeds said deviation threshold;

determining defect depth by analyzing temperature gradient between detection signals for a particular focal region;

identifying the defect by comparing said signature with known defect profiles stored in memory.

59. A method as claimed in claim 58 wherein, said method further involves spatially aligning consecutive transverse scan data.

60. A method as claimed in claim 58 wherein, said method further comprises:

opening the tracking file when a defect is detected; and mapping the defect in subsequent transverse scan data.

61. A method as claimed in claim 58 wherein, said method further comprises:

entering a learning mode when a particular detected defect fails to match known defect profiles stored in memory; and storing characteristics of the particular detected defect in memory.

62. A method as claimed in claim 58 wherein, said method further comprises:

performing noise reduction on said detected signals.

* * * * *